United States Patent
Colleran

(10) Patent No.: US 6,258,126 B1
(45) Date of Patent: *Jul. 10, 2001

(54) CUSHIONED JOINT PROSTHESIS

(75) Inventor: Dennis P. Colleran, Plainville, MA (US)

(73) Assignee: Depuy Orthopaedics, Inc., New Brunswick, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/929,223

(22) Filed: Sep. 9, 1997

(51) Int. Cl.$^7$ ........................................ A61F 2/38
(52) U.S. Cl. .............................. 623/20.29; 623/20.33
(58) Field of Search .................. 623/20, 18, 16

(56) References Cited

U.S. PATENT DOCUMENTS

| | | | | |
|---|---|---|---|---|
| 4,170,794 | * | 10/1979 | Zeibig et al. | 623/23 |
| 4,946,378 | * | 8/1990 | Hirayama et al. | 623/17 |
| 5,080,675 | | 1/1992 | Lawes et al. | 623/20 |
| 5,171,281 | | 12/1992 | Parsons et al. | 623/17 |
| 5,171,282 | * | 12/1992 | Pequignot | 623/20 |
| 5,507,823 | | 4/1996 | Walston et al. | 623/21 |
| 5,545,229 | | 8/1996 | Parsons et al. | 623/17 |
| 5,609,643 | | 3/1997 | Colleran et al. | 623/20 |
| 5,733,292 | * | 3/1998 | Gustilo et al. | 606/88 |

FOREIGN PATENT DOCUMENTS

| | | | |
|---|---|---|---|
| 8136619 | 5/1982 | (DE) . | |
| 40 06 714 A1 | * 9/1990 | (DE) | 623/20 |
| 42 28 710 A1 | * 3/1993 | (DE) | 623/18 |
| 0 046 926 | 8/1981 | (EP) . | |
| 0 447 065 | 9/1991 | (EP) . | |
| 2 642 301 A1 | * 8/1990 | (FR) | 623/20 |
| 2 682 285 A1 | * 4/1993 | (FR) | 623/18 |
| 2710837 | 10/1993 | (FR) . | |
| 9-164155 | * 6/1997 | (JP) | 623/20 |
| 94/02086 | * 2/1994 | (WO) | 623/20 |
| WO 94/26204 | 11/1994 | (WO) . | |
| 94/26204 | * 11/1994 | (WO) | 623/20 |

OTHER PUBLICATIONS

Concept Polymer Technologies, Inc., "C–FLEX", Concept Polymer Technologies, Inc., 12707 U.S. 19 So., Clearwater, FL 33546, a pamphlet consisting of a total of 12 unnumbered pages.

* cited by examiner

Primary Examiner—David H. Willse
(74) Attorney, Agent, or Firm—Nutter, McClennen & Fish, LLP

(57) ABSTRACT

A joint prosthesis includes a first prosthesis member having an inferior bone contacting surface, a second prosthesis having a superior bearing surface and a cushion member disposed between the two prosthesis members. The joint prosthesis is particularly useful for replacing bi-condylar joints and especially knee joints. The joint prosthesis is characterized by its high bearing surface contact area and low peak stress which is maintained even under malalignment conditions.

26 Claims, 7 Drawing Sheets

CUSHIONED JOINT PROSTHESIS

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates to a prosthesis having a component cushioned to absorb shock.

BACKGROUND OF THE INVENTION

Joint replacement surgery is quite common and enables many individuals to function normally when otherwise it would not be possible to do so. Artificial joints are normally composed of metallic and/or ceramic components that are fixed to existing bone.

Knee arthroplasty is a well known surgical procedure by which a diseased or damaged natural knee joint is replaced with a prosthetic knee joint. Typical knee prostheses include a femoral component, a patella component, a tibial tray or plateau, and a tibial bearing member. The femoral component generally includes a pair of laterally spaced apart condylar portions, the inferior or distal surfaces of which articulate with complementary condylar elements formed in a tibial bearing component. U.S. Pat. No. 5,609,643 provides an example of such a knee joint prosthesis and is hereby incorporated herein by reference.

In a properly functioning artificial knee joint, the condylar portions of the femoral component must slide and roll freely over the articulation surface formed by the condylar elements of the tibial bearing member. Natural friction within a replaced, artificial joint can lead to the development of wear debris in which minute particles of debris (e.g., metal or plastic from the prosthesis) become dislodged and migrate within the joint. The phenomenon of wear debris within artificial joints is a serious problem that can inhibit the proper mechanical functioning of the joint. Moreover, wear debris can lead to osteolysis and bone deterioration. When wear debris develops within an artificial joint, surgical removal of the debris or subsequent replacement of the artificial joint is often necessary.

Joint replacement surgery obviously requires a tremendous degree of precision to ensure that prosthetic components are properly sized, implanted, and aligned. The anatomy of patients who undergo knee arthroplasty is widely variable and can lead to difficulty in matching the standard sized prosthetic components that form a prosthetic joint. Imperfect sizing, implantation and alignment can lead to inadequate performance of the knee joint as well as to the presence of high contact stresses in certain areas of the prosthesis, thus leading to the possible development of wear debris.

During normal usage of a properly implanted prosthetic knee joint, load and stress are placed on the tibial bearing member. The tibial bearing member is typically made of an ultrahigh molecular weight polyethylene (UHMWPE), and friction, continuous cycling and stress can cause some erosion or fracture of the tibial bearing member, thus leading to wear debris. The risk of wear debris can be even greater during malalignment of an artificial knee joint, which can result from normal usage or from imperfect or inaccurate implantation of the prosthesis within a patient. Due to malalignment, the load on the tibial bearing member is not evenly distributed. Instead, excess load is placed on certain areas of the tibial bearing member. Even with the best available condyle designs, varus/valgus malalignment can lead to condylar lifting. That is, one of the femoral condyles is lifted from the tibial bearing member leaving all of the bearing load on one condyle. This uneven distribution of load can accelerate the development of wear debris. Contact stresses on the tibial bearing member increase the risk that wear debris will develop when a prosthetic knee joint is subjected to malalignment conditions.

In addition, conventional knee prostheses have no features which perform the load distribution functions of the medial and lateral menisci. These menisci absorb energy and distribute loads uniformly to the underlying bone. Without an energy absorbing mechanism in the knee prosthesis, shock loads are transmitted directly to the tibial tray-bone interface, leading to a loosening of the tibial tray component of the knee prosthesis. This loosening can lead to further malalignment and instability in the knee joint.

There is thus a need for knee joint prostheses that have a reduced tendency to develop wear debris due to the maintenance of good contact area and low contact stress between femoral and tibial components, even during the dynamics of daily activity and in various conditions of malalignment. There is further a need for knee joint prostheses that can distribute loads uniformly through the joint to the underlying bone.

SUMMARY OF THE INVENTION

The present invention provides a cushioned joint prosthesis. The prosthesis has a first prosthesis member, a second prosthesis member and a cushion member disposed between the two. The first prosthesis has an inferior surface which contacts a patient's existing bone, and a superior surface which mates with the cushion member. The second prosthesis member includes an inferior cushion contacting surface and an opposed, superior surface. In preferred embodiments, the first prosthesis member is at least partly formed from a biocompatible titanium alloy, the second prosthesis member is at least partly formed of ultrahigh molecular weight polyethylene and the cushion member is formed from an elastomeric polymer, such as a polysiloxane modified hydrocarbon block copolymer.

The cushioned joint prosthesis of the invention is also applied as an implantable knee joint prosthesis member. In this embodiment, the first prosthesis member is a tibial plateau having an elongate stem suitable for mounting on a patient's tibia. The second prosthesis member is a tibial bearing element having a superior femoral articulation surface with medial and lateral condylar elements.

The cushioned knee joint prosthesis embodiment of the invention may also be designed to be employed with existing modular knee replacement prostheses. For example, the cushion member may be disposed within a tibial bearing member for use with a conventional tibial tray.

The cushioned knee joint prosthesis of the invention may be characterized by its ability to distribute loads evenly despite varying degrees of varus/valgus malalignment. In particular, the contact stress on the articulation surface at a loading of 2060N with a varus/valgus malalignment of 3° remains below the yield strength of polyethylene.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
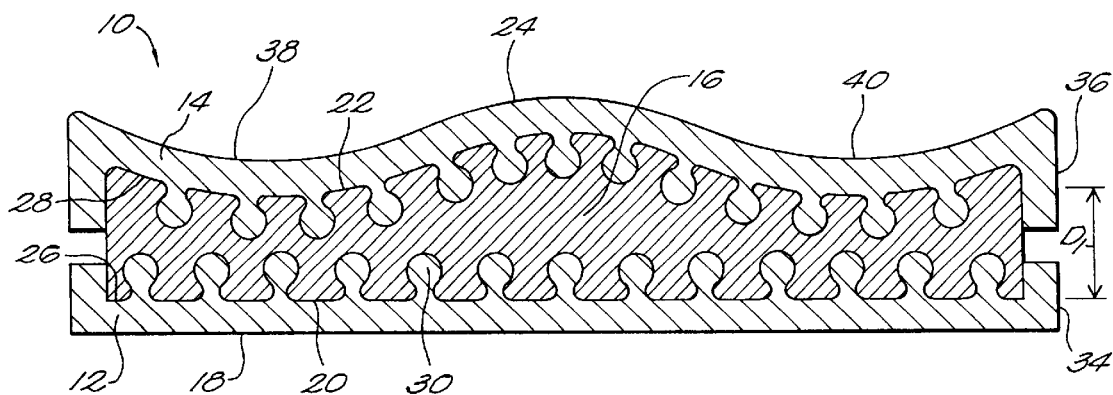
FIG. 1 is a cross-sectional view of a prosthesis of the invention.

A joint prosthesis 10 of the invention, illustrated in FIG. 1, has a first prosthesis member 12, a second prosthesis member 14 and a cushion member 16 disposed between the prosthesis members 12, 14. The first prosthesis member 12 has an inferior bone contacting surface 18 and a superior surface 20 upon which the cushion member 16 is mounted. The first prosthesis member 12 may be constructed from any material known by one of ordinary skill in the art to be useful for permanent implantation as a prosthesis. Exemplary materials include metals, such as titanium and titanium alloys, as well as polymeric materials such as ultrahigh molecular weight polyethylene.

The second prosthesis member 14 has an inferior cushion contacting surface 22 and an opposed superior bearing surface 24. The second prosthesis member 14 is mounted upon the cushion member 16 by means of its inferior cushion contacting surface 22. The second prosthesis member 14 may be constructed from materials useful in the construction of the first prosthesis member; the bearing surface 24 is however, preferably made from ultrahigh molecular weight polyethylene.

The cushion member 16 is constructed from an elastomeric material and has an inferior surface 26 and an opposed superior surface 28. The inferior surface 26 of the cushion member 16 contacts the first prosthesis member 22 while the superior surface 28 of the cushion member 16 contacts the second prosthesis member 14.

The elastomeric material utilized in the cushion member 16 may be any appropriate biocompatible elastomeric material. Suitable materials include thermoplastic elastomers such as those commercially available under the trademark C-Flex® (Concept, Inc.) or Pellethane® (Dow Chemical). A preferred thermoplastic elastomer for use in the present invention is a biocompatible polysiloxane modified styrene-ethylene/butylene (SEBS) block copolymer sold by Concept Polymer Technologies, Inc., Clearwater, Fla. under the C-Flex® trademark. This thermoplastic elastomer is also described in U.S. Pat. No. 4,511,354, which is hereby incorporated by reference. These elastomers are available or can be formulated so as to form final products of varying stiffness. The hardness of the cushion material for the prosthesis is chosen so that the composite prosthesis will reproduce the mechanical properties of the joint that it is designed to replace. Preferably, the elastomeric material or materials utilized for the cushion member 16 have a hardness in the range of 30 to 90 on the Shore-A hardness scale.

The cushion member 16 may be mated to the first and second prosthesis members 12, 14 using an appropriate biocompatible adhesive suitable for use in a prosthesis. Exemplary adhesives include medical device adhesives such as cyanoacrylate adhesives and medical-grade polyurethane adhesives. Alternatively, the cushion contacting surfaces 20, 22 of the first and second prosthesis members 12, 14 may be provided with a plurality of undercut anchors 30. The cushion member 16 then includes a plurality of corresponding depressions (not shown) on its inferior and superior surfaces 26, 28 that interlock with the undercut anchors 30 to mechanically mate the cushion member 16 with the prosthesis members 12, 14. The depressions in the cushion member 16 may be formed by molding the cushion material over the anchors 30. Of course, adhesive and mechanical mating means may be used solely or in combination.

Figure 2:
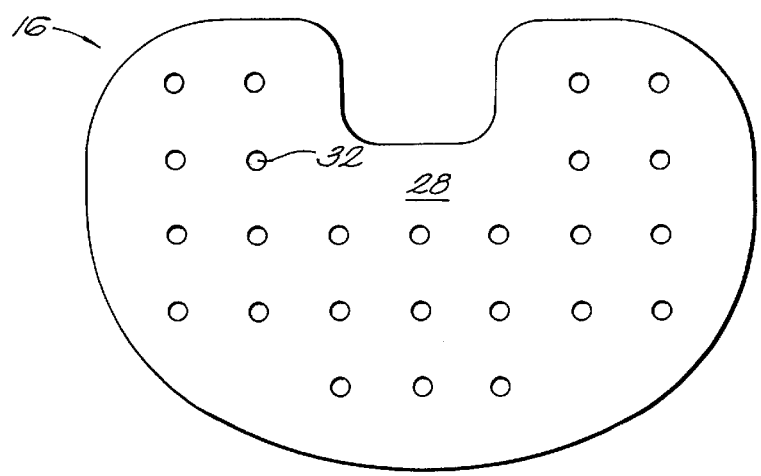
FIG. 2 is an elevated view of a cushion member useful with the invention.

The depth $D_1$ of the cushion member 16 may be constant across the cushion member 16, or it may vary as shown in FIG. 1. While the depth of the cushion member 16 may be selected by a person of ordinary skill in the art depending upon the particular application of the prosthesis 10, the minimum depth of the cushion $D_1$ is generally in the range of 2 to 6 mm. The cushion may also be provided with a plurality of relief holes 32 as shown in FIG. 2. These relief holes 32 provide clearance for the cushion member 16 to expand laterally in response to a compressive force or shock placed on the prosthesis 10.

The first and second prosthesis members 12, 14 may also be provided with circumferential rims 34, 36 that contact the cushion member 16 about its circumference. The circumferential rims 34, 36 localize shearing forces created by twisting moments placed on the prosthesis 10 within the cushion member 16. This localization allows the cushion member 16 to absorb rotational shocks to the prosthesis 10 as well as longitudinal shocks. In addition, the shear forces act within the cushion member 16 rather than on one of its surfaces 26, 28 where the shear forces would tend to separate the cushion member 16 from the prosthesis members 12, 14.

The prosthesis 10 of the invention serves particularly well in the replacement or augmentation of bi-condylar joints. When used in such joints, the superior bearing surface 24 of the second prosthesis member 14 is a condylar articulation surface having medial and lateral condylar elements 38, 40. Preferably, the cushion member 16 mates with the inferior surface 28 of the second prosthesis member 14 opposite both the medial and lateral condylar elements 38, 40.

Figure 3:
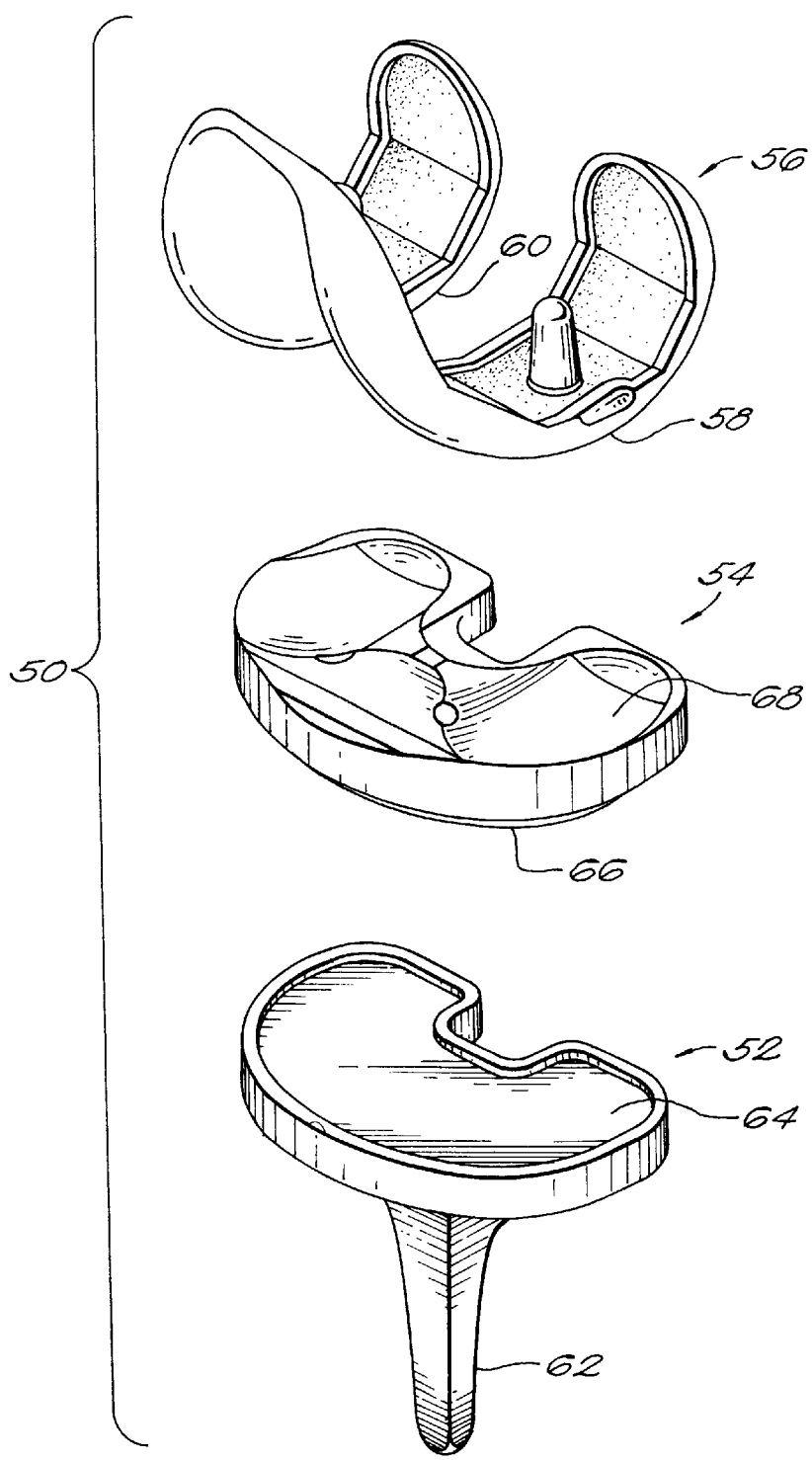
FIG. 3 is an exploded view of a prior art knee joint prosthesis.

The prosthesis of the invention is particularly useful as a tibial component of a knee joint prosthesis. An exemplary knee joint prosthesis 50, shown in FIG. 3, typically comprises a tibial tray 52, a tibial bearing insert 54 and a femoral component 56 having two femoral condyle elements 58, 60. As used herein, the term "standard tibial tray" refers to a tibial component such as the tibial tray 52 having an inferior stem 62 for attaching the prosthesis to a patient's tibia and a superior plateau 64 for receiving the tibial bearing insert 54. The standard tibial tray does not contain a cushion. The term "standard tibial bearing insert," as used herein, refers to a bearing insert such as the tibial bearing insert 54 having an inferior tibial tray contacting surface 66 and a superior tibial bearing surface 68 suitable to articulate with femoral condylar elements 58, 60. The standard tibial bearing insert also does not include a cushion. U.S. Pat. No. 5,609,643 provides examples of non-cushioned knee prostheses having superior tibial and femoral articulation surfaces.

Figure 4:
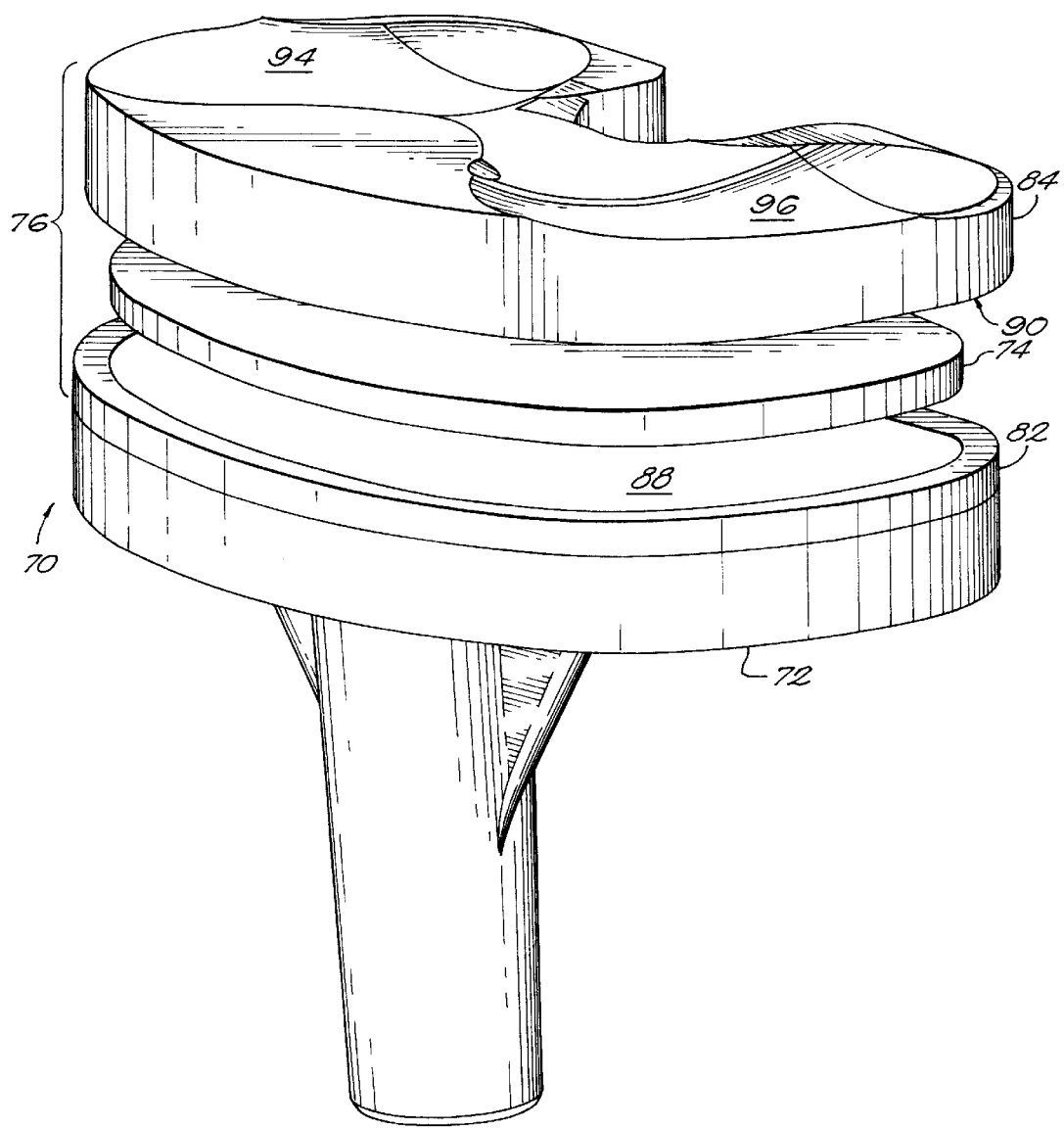
FIG. 4 is an exploded view of a tibial component embodiment of the invention.
Figure 5:
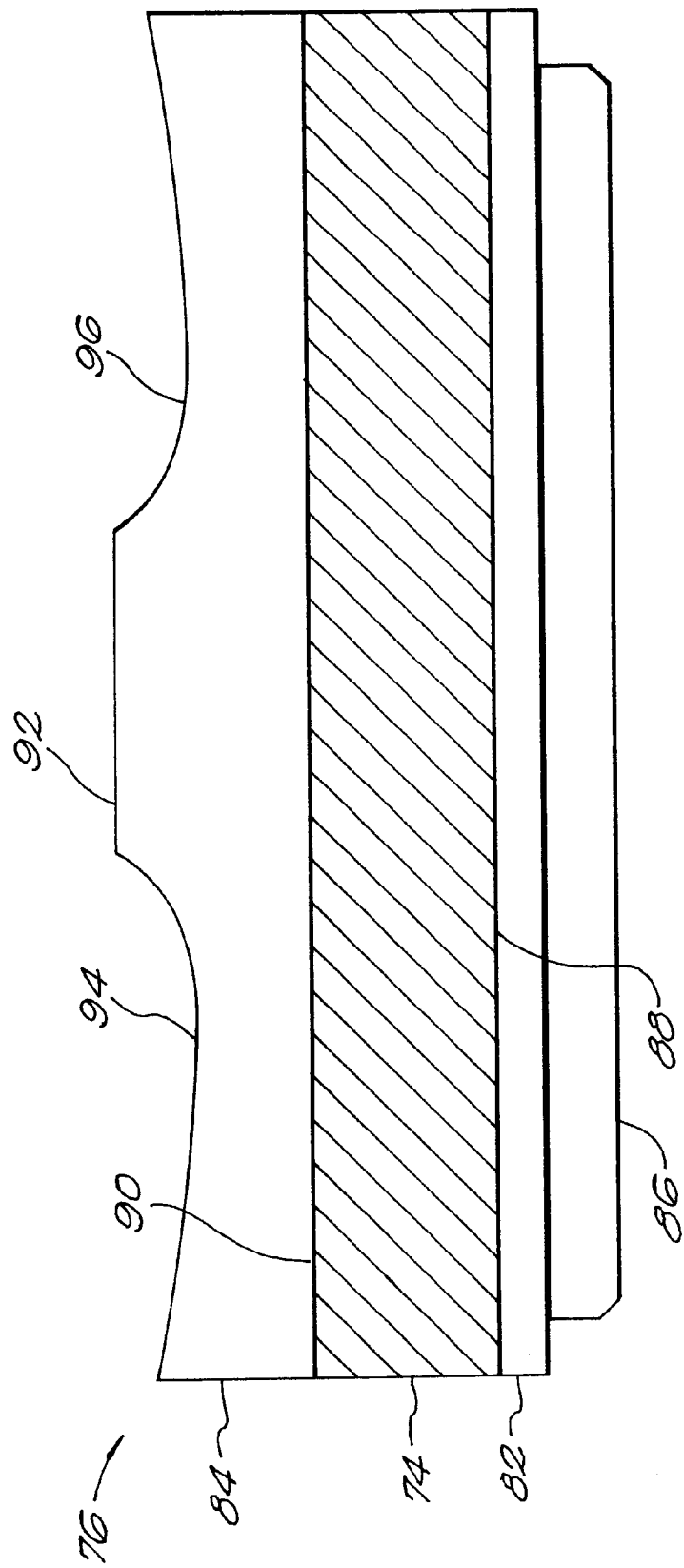
FIG. 5 is a side view of a tibial bearing member of the prosthesis of FIG. 4.
Figure 6:
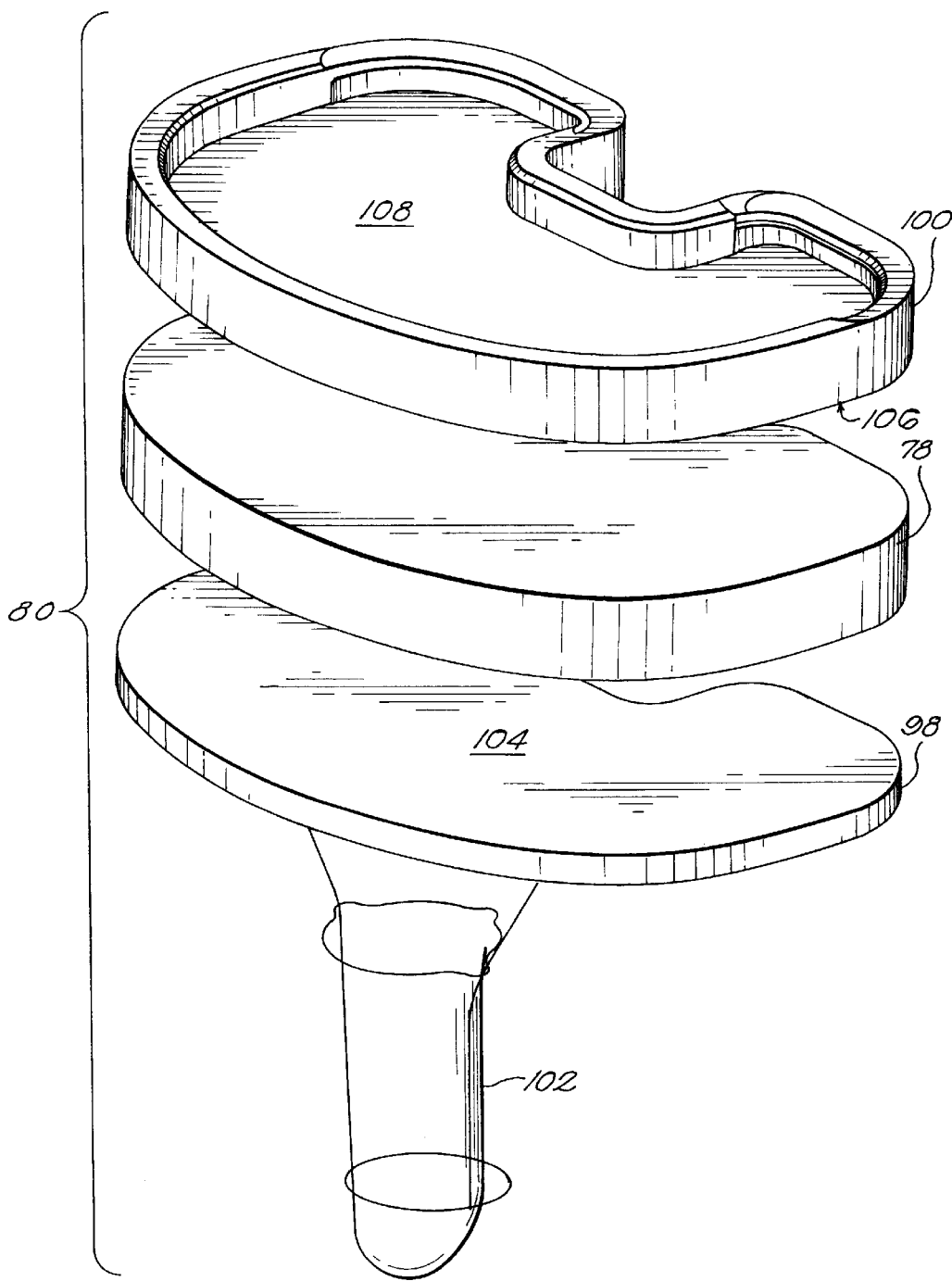
FIG. 6 is an exploded view of an alternative tibial component embodiment of the invention.

Specific embodiments of a prosthesis of the invention as a tibial component of a knee joint prosthesis are illustrated in FIGS. 4 through 6. In the embodiment of FIGS. 4 and 5, tibial component 70 includes a standard tibial tray 72 and a cushion member 74 is located within a tibial bearing component 76. In FIG. 6, a cushion member 78 is located within a tibial tray component 80 and a standard tibial bearing insert may be mounted upon the tibial tray component 80. Of course, tibial components of the invention need not use standard tibial trays or bearing inserts. For example, a cushion member may be provided directly on a tibial plateau and have a bearing surface mounted directly upon the cushion member. One of ordinary skill in the art will readily recognize that other configurations of a tibial component of the invention are possible.

The tibial bearing component 76 illustrated in FIGS. 4 and 5 includes first and second bearing elements 82, 84 as well as cushion member 74. The first bearing element 82 has an inferior tibial tray contacting surface 86 and a superior cushion contacting surface 88. The tibial tray contacting surface 86 may be adapted to seat upon the superior plateau 64 of tibial tray 52 (shown in FIG. 3). The second bearing element has an inferior cushion contacting surface 90 and an opposed superior femoral articulation surface 92 having medial and lateral articulation elements 94, 96. The medial and lateral articulation elements 94, 96 articulate with femoral condyles or with the condyles of a femoral prosthesis such as lateral and medial condyles 60, 58 of the femoral component 56 shown in FIG. 3.

The cushion member 74 is disposed between the first and second bearing elements 82, 84. The cushion member 74 may be constructed from the same materials and may have the same features described with respect to cushion member 16 above. The cushion member 74 may mate with the bearing elements 82, 84 using a mechanical interlock or adhesives as with the cushion member 16. Further, the cushion means 74 may include relief holes, such as relief holes 32, and may preferably have a minimum depth of 2 to 6 mm.

The tibial component 80, shown in FIG. 6, has a first tibial tray element 98, a second tibial tray element 100 and a cushion member 78 disposed between the tibial tray elements 98, 100. The first tibial tray element 98 has an elongate stem 102 suitable for mating with a patient's tibia and a plateau surface 104 that mates with the cushion member 78. The second tibial tray element 100 has an inferior cushion means contacting surface 106 and an opposed tibial bearing insert receiving surface 108. The tibial bearing insert receiving surface may be adapted to receive a standard tibial bearing insert such as tibial bearing insert 54. The cushion member 78 may be the same as cushion member 74 described above.

Figure 8:
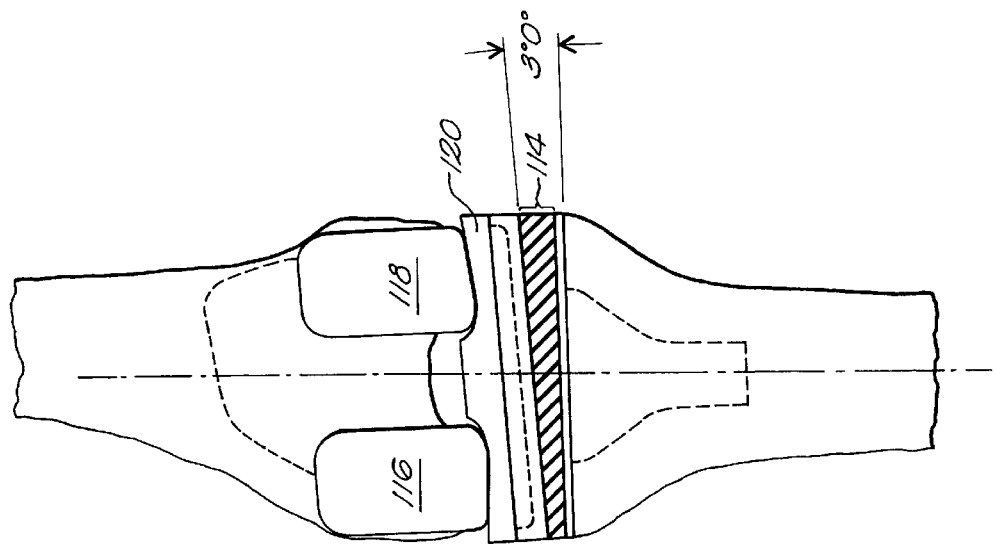
FIG. 8 is a posterior view of an implanted cushioned knee joint prosthesis of the invention with a varus/valgus malalignment of 3°.
Figure 7:
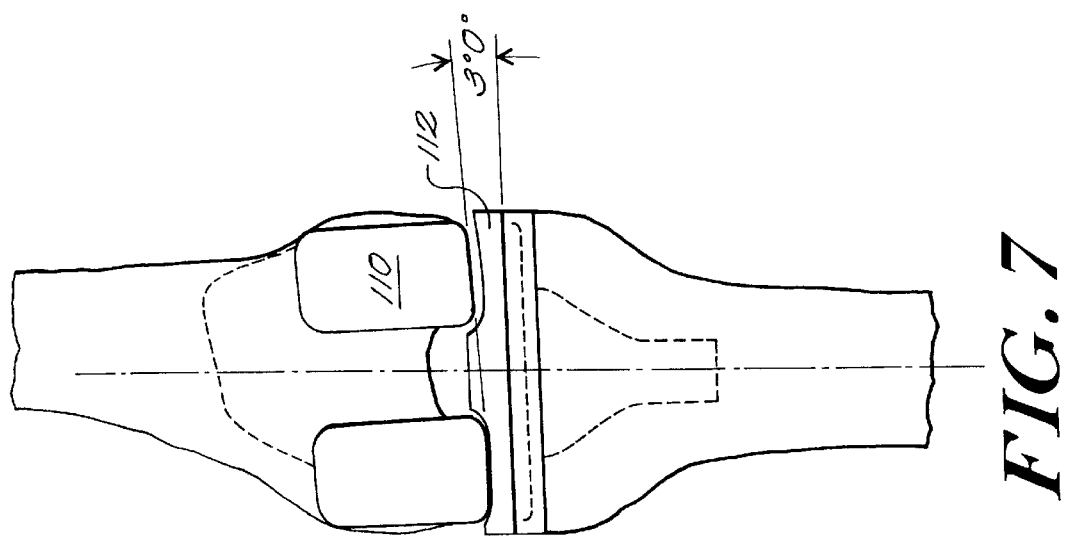
FIG. 7 is a posterior view of an implanted conventional modular knee joint prosthesis with a varus/valgus malalignment of 3°.

One distinguishing feature of a prosthesis of the invention is the ability of the prosthesis to maintain a high degree of contact between its bearing surface and the opposed bone or prosthesis even in a condition of joint malalignment. A posterior view of a conventional knee joint prosthesis is depicted in FIG. 7 as implanted in a patient under a varus/valgus malalignment of 3°. One can readily see that the medial femoral condyle 110 of this prosthesis has lifted from the bearing element 112. FIG. 8 provides a similar view of a knee joint prosthesis having a tibial component of the invention (having a cushion means 114) under the same 3° varus/valgus malalignient condition. Here, both femoral condyles 116, 118 remain in contact with the bearing element 120 despite the malalignient condition. A knee joint prosthesis having a tibial component of the present invention has significantly increased surface contact area over many known knee joint prostheses under these conditions.

Figure 9:
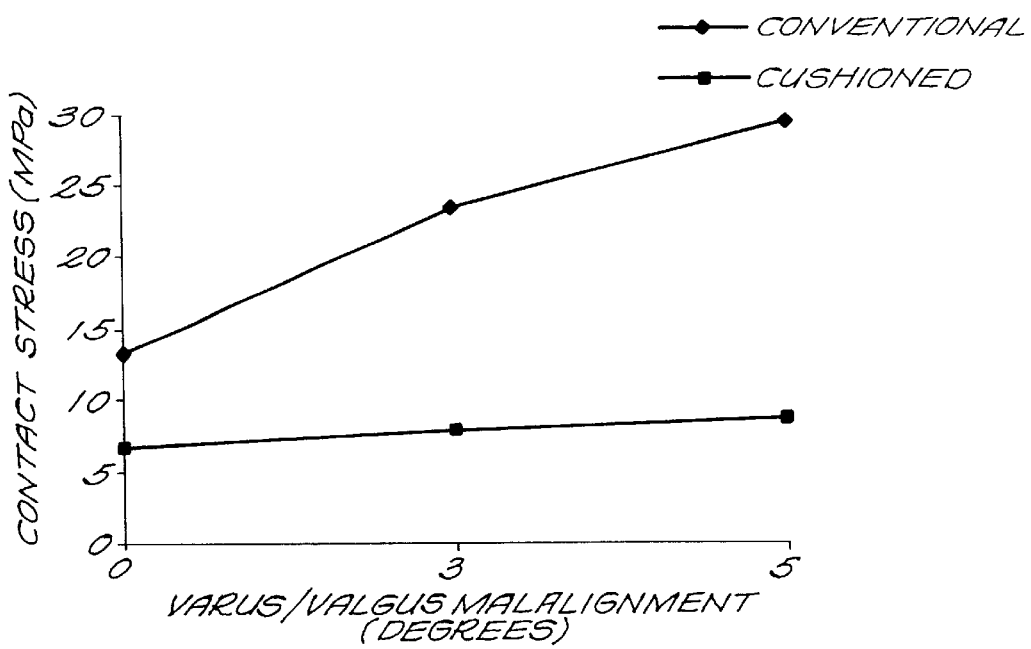
FIG. 9 is a plot showing observed contact stress values for a conventional modular knee joint prosthesis and a cushioned knee joint prosthesis of the invention at varying degrees of varus/valgus malalignment.

FIG. 9 illustrates observed values of contact stress between the articulation surfaces of a femoral component and a tibial bearing member for a prior art knee prostheses and a knee prosthesis of the present invention. To generate the data shown in FIG. 9, contact stress was evaluated for a knee prosthesis in an alignment condition of 15° flexion; 0°, 3° and 5° varus-valgus lift; and 0° internal-external rotation when subjected to a load of about 2060 N, approximately three times average body weight.

The experimental protocol required that the femoral components be cemented to an appropriate holding block by forcing the femoral component onto the block (which bears a cement) until the femoral component can move no further. Tibial trays are then cemented onto tibial holding blocks. A rotary indexing table is then fastened onto a x-ray plate which is bolted to an Instron 1123 tensile compressive mechanical testing machine. The rotary indexing table is leveled and shimmed, if necessary. This apparatus is attached to the Instron 1123 in an orientation rotated approximately 45° clockwise from the anterior forward position.

The femoral test block is then fastened to a femoral block holding bracket and this assembly is screwed into the load cell of the Instron 1123. Next, the tibial holding block is bolted onto the base plate of the rotary indexing table. The femoral assembly (without the femoral components attached) is placed against the tibial holding block. The femoral assembly should be adjusted such that the tibial holding block is perpendicular to the femoral block holder. (The rotary dial is not used in the alignment process.)

Prior to testing, the tibial inserts are soaked in a water bath (37° C.±1° C.) for about 18–24 hours. The tests are conducted within an environmental chamber which is at a temperature of 37° C.±1° C. and at 80–90% relative humidity. When the chamber reaches the desired temperature and humidity levels, the tibial insert is removed from the bath and inserted into the tibial holding fixture. During testing the femoral component can be set at a desired flexion angle.

At the outset of testing a crosshead speed of 2 mm/minute, with a 500 kg full scale setting on the Instron chart recorder, is set. An interpositional film having an electrode sensor grid, such as TEKSCAN, available from Tekscan, Inc. of Boston, Mass., is then placed between the femoral and tibial components. The real time screen is opened and the force calibration is performed. The sensor is placed between the femoral component and the tibial insert. Loading is ideally located at the center of the sensor grid. The TEKSCAN technology then prompts the user to enter the load value applied. Next, the femoral is loaded onto the tibial insert (and the TEKSCAN sensors). The load is allowed to increase until the appropriate level is reached. At that instant, the "stop" button on the Instron displacement controller and the "Enter" key on the PC keyboard are depressed simultaneously. The contact stress and contact area are recorded and the load is then removed.

As illustrated, the cushioned prosthesis of the present invention exhibited peak contact stress well below that of prior art modular knee prosthesis. The knee prosthesis of the present invention displayed contact stress of approximately 6.7 to 8.8 MPa as the varus/valgus lift increased from 0° to 5°, while contact stress for prior art knee prosthesis ranged from 13.4 to 29.5 MPa. The contact stresses measured and reported are peak contact stresses for one condylar bearing surface where only one condyle contacted the bearing surface, and an average of the peak contact stresses for each condylar surface where both condyles contacted the bearing surface.

Figure 10:
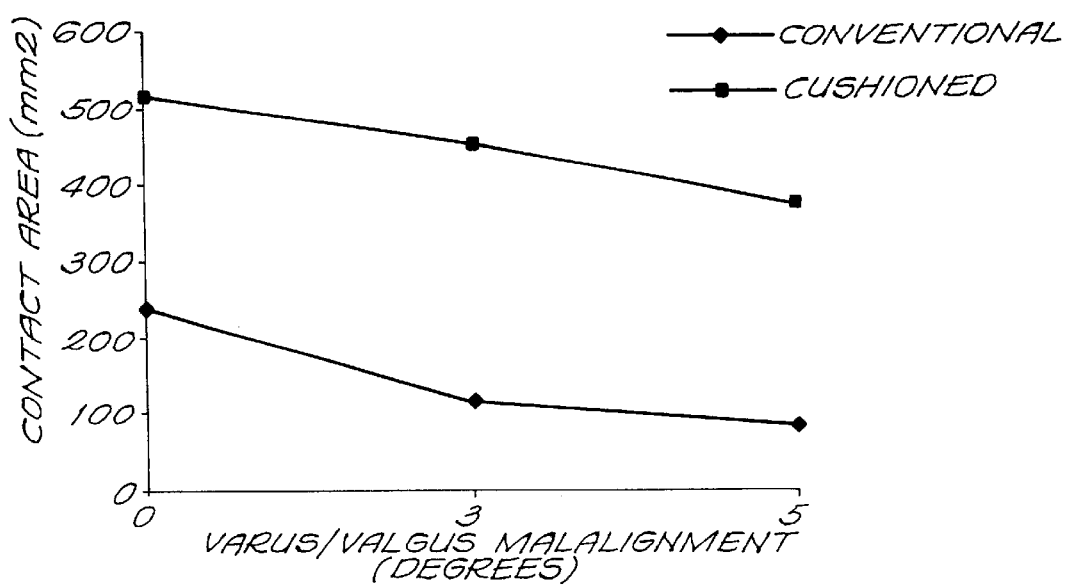
FIG. 10 is a plot showing observed contact areas between femoral condyles and tibial bearing surfaces for a conventional modular knee joint prosthesis and a cushioned knee joint prosthesis of the invention at varying degrees of varus/valgus malalignient.

FIG. 10 illustrates data obtained while comparing the contact are between femoral and tibial components of the prostheses under the same conditions described with respect to FIG. 9. The data shown in FIG. 10 was also generated using the procedure described above as the TEKSCAN technology provides both contact area and contact stress in defined areas of a knee joint prosthesis.

At a 0° varus/valgus malalignment, the cushioned knee joint prosthesis of the invention has approximately double the contact area and half the peak stress of the prior art modular knee joint prosthesis. As varus/valgus malalignment is introduced and increased, the differences become even more pronounced. Significantly, the peak contact stress for the cushioned knee joint prosthesis remains below the yield strength of polyethylene (approximately 12 MPa) despite the varus/valgus malalignment and the substantial load (2060N—approximately three times standard body weight) tested.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A joint prosthesis system, comprising:
a femoral component having medial and lateral articulation surfaces;
a first prosthesis member having a superior surface and an inferior bone contacting surface;
a cushion member mounted upon the superior surface of the first prosthesis member, the cushion member being formed of an elastomeric material and having an inferior surface and an opposed superior surface; and
a second prosthesis member separate from, and movable with respect to the first prosthesis member, the second prosthesis member comprising a bicondylar bearing member having an inferior, cushion contacting surface mounted upon the superior surface of the cushion member and an opposed superior substantially rigid articulation surface having medial and lateral articulation surfaces;
wherein the second prosthesis member is unconnected to, but in contact with the femoral component such that the femoral component maintains an articulating relationship with the second prosthesis member medial and lateral articulation surfaces; and
wherein the second prosthesis member moves in response to varus/valgus malalignment conditions of up to at least 3° so as to maintain contact between the second prosthesis member and the femoral component at both the medial and lateral articulation surfaces.

2. The joint prosthesis system of claim 1, wherein the first prosthesis member comprises a biocompatible metal.

3. The joint prosthesis system of claim 2, wherein the biocompatible metal is a titanium alloy.

4. The joint prosthesis system of claim 2, wherein the second prosthesis member comprises ultrahigh molecular weight polyethylene.

5. The joint prosthesis of claim 1, wherein the elastomeric material is a polysiloxane modified hydrocarbon block copolymer.

6. The joint prosthesis system of claim 1, wherein the cushion member is mated to the first and second prosthesis members using a biocompatible adhesive.

7. The joint prosthesis system of claim 1, wherein the superior surface of the first prosthesis member and the inferior surface of the second prosthesis member each have a plurality of undercut anchors and the cushion member includes a plurality of depressions interlockable with the undercut anchors so as to mechanically mate the cushion member to the first and second prosthesis members.

8. The joint prosthesis system of claim 1, wherein the cushion member has a minimum depth of about 2 to 6 mm.

9. The joint prosthesis system of claim 8, wherein the cushion elastomer has a rating of about 30 to 90 on the Shore-A hardness scale.

10. The joint prosthesis of claim 1, wherein the superior articulation surface of the second prosthesis member comprises medial and lateral condylar elements.

11. The joint prosthesis system of claim 10, wherein the cushion is mated to the second prosthesis member opposite both the lateral and medial condylar elements.

12. The joint prosthesis of claim 11, wherein the first prosthesis member comprises a tibial plateau.

13. The joint prosthesis system of claim 12, wherein the inferior surface of the first prosthesis member comprises an elongate stem suitable for mounting on a patient's tibia.

14. The joint prosthesis system of claim 13, wherein contact stress on the articulation surface at a loading of 2060N with a varus/valgus malalignment of 3° remains below the yield strength of ultra high molecular weight polyethylene.

15. A joint prosthesis system, comprising:
a femoral component having medial and lateral articulation surfaces;
a first bearing element having an inferior tibial plateau contacting surface and an opposed superior cushion contacting surface;
a second bearing element separate from, and movable with respect to the first bearing element, the second bearing element having an inferior cushion contacting surface and an opposed superior substantially rigid articulation surface having medial and lateral articulation surfaces; and
a cushion means disposed between the first and second bearing elements for absorbing and distributing load;
wherein the second bearing element is unconnected to, but in contact with the femoral component such that the femoral component maintains an articulating relationship with the second bearing element medial and lateral articulation surfaces; and
wherein the second bearing element moves in response to varus/valgus malalignment conditions of up to at least 3° so as to maintain contact between the second bearing element and the femoral component at both the medial and lateral articulation surfaces.

16. The joint prosthesis system of claim 15, wherein the first prosthesis member and the second prosthesis member each have circumferential rims that extend in the direction of the cushion member and contact the cushion member around a circumference thereof.

17. A tibial bearing element for a knee prosthesis, comprising:
   a first bearing element having an inferior tibial plateau contacting surface and an opposed superior cushion contacting surface;
   a second bearing element having an inferior cushion contacting surface and an opposed superior substantially rigid femoral articulation surface having medial and lateral articulation elements; and
   a cushion means lisposed between the first and second bearing elements for absorbing and distributing load;
   wherein the second bearing element is separate from, and movable with respect to the first bearing element.

18. The tibial bearing element of claim 17, wherein the cushion means is formed from an elastomeric material.

19. The tibial bearing element of claim 18, wherein the elastomeric material is a polysiloxane modified hydrocarbon block copolymer.

20. The tibial bearing system of claim 18, wherein the cushion means includes a plurality of relief holes extending fully therethrough.

21. The tibial bearing element of claim 20, wherein the superior surface of the first bearing element and the inferior surface of the second bearing element each have circumferential rims that extend in the direction of the cushion means and contact the cushion means around a circumference thereof.

22. The tibial bearing element of claim 18, wherein the cushion means is mated to the first and second bearing elements using a biocompatible adhesive.

23. The tibial bearing element of claim 18, wherein the superior surface of the first bearing element and the inferior surface of the second bearing element each include means for mechanically interlocking with the cushion means to mechanically mate the cushion means to the first and second bearing elements.

24. The tibial bearing element of claim 18, wherein the cushion means has a minimum depth of about 2 to 6 mm.

25. The tibial bearing element of claim 24, wherein the cushion elastomer has a rating of about 30 to 90 on the Shore-A hardness scale.

26. The tibial bearing element of claim 25, wherein the contact stress on the articulation surface at a loading of 2060N with a varus/valgus malalignment of 3° remains below the yield strength of ultra high molecular weight polyethylene.

* * * * *